United States Patent [19]

Sisti et al.

[11] Patent Number: 5,914,411

[45] Date of Patent: Jun. 22, 1999

[54] ALTERNATE METHOD FOR ACYLATING 10-DEACETYLBACCATIN III SELECTIVELY AT THE C-10 POSITION

[75] Inventors: Nicholas J. Sisti; Jan Zygmunt, both of Boulder; Herbert R. Brinkman, Superior; Madhavi C. Chander, Boulder; Xian Liang, Boulder; James D. McChesney, Boulder, all of Colo.

[73] Assignee: NaPro BioTherapeutics, Inc., Boulder, Colo.

[21] Appl. No.: 09/010,285

[22] Filed: Jan. 21, 1998

[51] Int. Cl.⁶ .................................................. C07D 305/14
[52] U.S. Cl. ............................................ 549/510; 549/511
[58] Field of Search ...................... 549/510, 511

[56] References Cited

U.S. PATENT DOCUMENTS 5,229,526   7/1993   Holton ..................................... 549/213

OTHER PUBLICATIONS

Kant et al, "A Chemoselective Approach to Functionalize the C–10 Position of 10–Deacetylbaccatin III. Synthesis and Biological Properties of Novel C–10 Taxol Analogues", Tetrahedron Letters, 35 (31), pp. 5543–5546, 1994.

*Primary Examiner*—Ba K. Trinh
*Attorney, Agent, or Firm*—Timothy J. Martin; Michael R. Henson; Mark H. Weygandt

[57] ABSTRACT

A method of acylating 10-deacetylbaccatin III at the C-10 position over the C-7 hydroxy position thereof to produce baccatin IIII is accomplished first by dissolving 10-deacetylbaccatin III in an acceptable ether solvent therefor, such as tetrahydrofuran. A lithium salt, preferably lithium chloride, is added. A trialkylamine base or pyridine is next added, followed by the addition of an acylating agent, such as acetyl chloride. The resulting solution may be quenched, for example with ammonium chloride, to eliminate excess of the acylating agent. The result is baccatin III in solution. This solution may then be diluted with ethyl acetate to form an organic phase and an aqueous phase, with the organic phase being washed and thereafter reduced. Recrystallization and column chromatography may be employed to purify the baccatin III.

29 Claims, No Drawings

ALTERNATE METHOD FOR ACYLATING 10-DEACETYLBACCATIN III SELECTIVELY AT THE C-10 POSITION

FIELD OF THE INVENTION

The present invention broadly concerns taxane chemistry. Broadly, the present invention is directed to the acylation of 10-deacetylbaccatin III at the C-10 position over the C-7 position. The present invention especially concerns the acylation of 10-deacetylbaccatin III to provide baccatin III.

BACKGROUND OF THE INVENTION

Taxane compounds have received increasing attention among the scientific and medical community because of indications that various ones of these compounds, including paclitaxel (referred to in the literature as "taxol"), docetaxel (TAXOTERE®) and others, exhibit anti-tumor activity.

Paclitaxel is a naturally occurring taxane diterpenoid which is found in several species of the Yew (genus taxus, Family Taxaceae). Unfortunately, the concentration of this compound is very low. While the presence of this compound is found in the yew tree at extremely low concentrations, there are many other taxane compounds, especially 10-deacetylbaccatin III, which are able to be extracted in relatively high concentrations from renewable portions of the yew. 10-deacetylbaccatin III has the general formula:

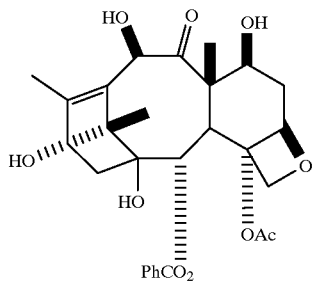

In an effort to increase the available supply of the anti-tumor compounds, efforts have been made to partially synthesize the paclitaxel, docetaxel and other analogs by joining a chiral, non-racemic side chain and a protected baccatin III backbone. In some instances, it is preferable to start with baccatin III as the backbone unit while in other instances, it is possible to use 10-deacetylbaccatin III as the starting backbone unit. Baccatin III, which has the formula as follows:

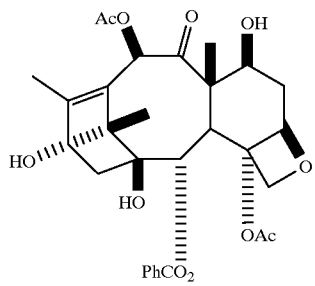

is differentiated from 10-deacetylbaccatin III by the presence of the acetate group at the C-10 location.

There have been efforts reported in the past to acylate 10-deacetylbaccatin III to provide baccatin III, but these efforts have met with mixed results. It may be observed that the 10-deacetylbaccatin III molecule has four hydroxy positions, at C-1, C-7, C-10 and C-13. A first impression from a review of this molecule would suggest that the hydroxyl positions would all be statistically acylated by an acylating compound. However, this is not true due to the steric environment of the C-1 and C-13 sites. Indeed, the hydroxy group at C-1 is so sterically encumbered that essentially no acylation would ordinarily occur at this position. Moreover, the hydroxy group at C-13 is the next most encumbered position, and it is difficult to acylate at the C-13 site. It is for this reason that the esterification of a protected baccatin III backbone with the phenylisoserine side chain, for example, has proved difficult because the C-13 hydroxy group is located within the concave region of the hemispherical taxane skeleton, thus making it difficult to access. Accordingly, attempts to acylate 10-deacetylbaccatin III results in little acylation at the C-13 position.

Reactions at the C-7 and C-10 hydroxy positions on the 10-deacetylbaccatin III molecule are quite different as these sites are dramatically more reactive than those at C-1 and C-13. Of the two sites, it has been observed that the C-7 site is more reactive. The results of attempted acylation of the 10-deacetylbaccatin III molecule using pyridine with a large excess of an acylating agent such as acetyl chloride as reported in Denis et al, "A Highly Efficient, Practical Approach to Natural Taxol", *Journal of the American Chemical Society*, 1988, 110, 5917. As reported in this journal article, acylation was most favored at the C-7. Acylation at C-7, of course, is highly undesirable because once acylated, it has not been demonstrated that the acetyl group at C-7 can be selectively removed thus making the compound undesirable as a precursor to any known anti-neoplastic taxane. Moreover, any selective acylation at C-10 is in extremely small quantities so as to produce a small yield.

As a result of the reactivity of the C-7 hydroxy position, attempts at converting 10-deacetylbaccatin III to baccatin III have been directed to a first step of selectively protecting the 10-deacetylbaccatin III molecule at the C-7 hydroxy position, for example, with a triethylsilyl (TES) group. This technique is reported in the Denis et al article, cited above. As described, 10-deacetylbaccatin III is converted to C-7 TES-protected 10-deacetylbaccatin III followed by the acylation of the compound at the C-10 location. Here, 10-deacetylbaccatin III is reacted with a large excess of TES-Cl and pyridine.

Alternatively, C-7 TES-protected baccatin III may be produced according to a procedure described in Kant et al "A Chemo-Selective Approach To Functionalize The C-10 Position of 10-deacetylbaccatin III Syntheses and Biological Properties of Novel C-10 Taxol® Analogs", *TETRAHEDRON LETTERS*, Volume 35, No. 31, TP 5543–5546 (1994). In this article, 10-deacetylbaccatin III is mixed with dimethylformamide (DMF) under a nitrogen atmosphere, and imidazole is added while stirring. TES-Cl is added dropwise followed by a quenching of the mixture. After obtaining the C-7 TES protected 10-deacetylbaccatin III, it is then acylated at C-10 using n-butyl lithium or lithium hexamethyl disilizane and acetyl chloride. The resulting C-7 TES-protected baccatin III is then deprotected at the C-7 position by any convenient method. An example of such a method uses aqueous hydrochloric acid. However, in the semi-syntheses of paclitaxel, deprotection usually is performed only after attaching the phenylisoserine side chain so that 10-deacetylbaccatin III is not converted directly into baccatin III. Previously I have reported in Method for Selective Acylation of 10-Deacetylbaccatin III, Ser. No. 08/678,759 now U.S. Pat. No. 5,750,736, a method to convert 10-deacetylbaccatin III directly to baccatin III utilizing n-butyl lithium and acetyl chloride in tetrahydrofuran at low temperature.

SUMMARY OF THE INVENTION

It is an object of the present invention to provide a new and useful method for the conversion of 10-deacetylbaccatin III into the baccatin III molecule.

Another object of the present invention is to provide a simple chemical route from 10-deacetylbaccatin III to baccatin III which avoids the necessity of protecting the C-7 hydroxy position of 10-deacetylbaccatin III and the deprotection thereof following the step of acylating at the C-10 position.

A further object of the present invention is to provide an efficient method for producing good yields of baccatin III from 10-deacetylbaccatin III.

Still a further object of the present invention is to provide a relatively inexpensive process for the production of baccatin III from the more abundant 10-deacetylbaccatin III which may be used in commercial processes, including the semi-synthesis of paclitaxel and its analogs.

According to the present invention, then, a method is described for producing baccatin III from 10-deacetylbaccatin III. This method comprises a first step of dissolving a selected quantity of 10-deacetylbaccatin III in an acceptable ether solvent to form a first solution. Next, a solution containing a lithium salt, preferably lithium chloride in tetrahydrofuran, is mixed into the first solution to form a second solution. Next, a base selected from a group consisting of trialkyl amine bases and pyridine is added to the second solution to form a third solution. Next, an acylating agent, preferably acetyl chloride, is combined with the third solution to form a fourth solution.

In this method, it is preferred that approximately one equivalent of the lithium salt in solution is added to the first solution to form the second solution. However, the lithium salt may be in a range of approximately one to two equivalents thereof. It is also preferred that approximately five equivalents of the base be added to the second solution to form the third solution although between two and ten equivalents of the base may be added. This base is preferably triethyl amine.

The third solution may be added to a solution containing between two and ten equivalents of the acylating agent to form the fourth solution. Preferably approximately five equivalents of the acylating agent are dissolved in tetrahydrofuran into which the third solution is added to form the fourth solution. This fourth solution is then stirred for an interval of one-half to twenty-four hours, although higher yields are present at the longer duration.

The method according to the present invention can be continued by quenching the fourth solution with a suitable quenching compound that is effective to eliminate excess of the acylating agent therefrom thereby to produce a fifth solution. The fifth solution may be diluted with ethyl acetate to form an organic phase and an aqueous phase. Thereafter, the organic phase may be washed with one normal HCl and brine and thereafter reduced to a first residue. This first residue may be purified, such as by column chromatography, recrystallization and the like, to afford baccatin III.

The 10-deacetylbaccatin III is preferably dissolved in an ether solvent selected from a group consisting of tetrahydrofuran and polyethers. It is preferred that the ether solvent be anhydrous. The preferred acylating agent is acetyl chloride and the preferred quenching compound is ammonium chloride solution. The steps of the method are performed, preferably at a temperature between −10° C. and 30° C. although the preferred temperature is approximately 25° C. The preferred lithium salt is lithium chloride.

These and other objects of the present invention will become more readily appreciated and understood when the following detailed description of the exemplary embodiment is considered.

DETAILED DESCRIPTION OF THE EXEMPLARY EMBODIMENT

The present invention broadly concerns the conversion of 10-deacetylbaccatin III into baccatin III without the need to protect the reportedly more reactive C-7 position of the 10-deacetylbaccatin III molecule. The present method has been found to surprisingly produce high yields of baccatin III directly from 10-deacetylbaccatin III with the yields typically being on the order of eighty percent of baccatin III with five percent being the C-7 acetate of baccatin III. This result is unexpected due to the general belief that the C-7 hydroxy position is more reactive and thus selectively acylates in preference to the C-10 hydroxy site. However, the present process indicates that selective acylation at the C-10 hydroxy position of the 10-deacetylbaccatin III molecule can occur without significant amounts of the detrimental acylation at the C-7 position when the reaction takes place in the presence of a trialkyl amine base or pyridine, preferably triethylamine, and a lithium salt preferably lithium chloride.

The reaction according to the present invention may be diagrammed as follows:

Here, a selected quantity of 10-deacetylbaccatin III is dissolved in an acceptable ether solvent to form a first solution at a first temperature. The preferable ether solvent is tetrahydrofuran (THF). This step is conducted under a nitrogen atmosphere, and it is desirable that the solvent be anhydrous since the presence of water or humidity can impede or destroy the ability for the reaction to proceed. The step of dissolving the 10-deacetylbaccatin III is preferably done at temperature of −10° to 30° C. although it is preferred that the first temperature be about 25°.

Next, a solution of lithium chloride in tetrahydrofuran is added to the first solution at a first temperature to form a second solution at the first temperature. It is preferable that about 1.1 equivalents of lithium chloride in the THF be used although at least about one equivalent of lithium chloride in THF is added to the first solution with an acceptable range being about one to two equivalents of the lithium chloride in THF. Reducing the amount of the lithium salt, while effective to produce the desired reaction, will nonetheless reduce the yield with less selectivity. Excess lithium chloride in THF beyond this range would have little effect.

Next, a trialkyl amine base or pyridine, preferably triethyl amine, is added to the second solution at the first temperature to form a third solution at the first temperature. It is preferable that about five equivalents of triethylamine be used although at least two equivalents of triethylamine base is added to the second solution at the first temperature with an acceptable range being two to ten equivalents of triethylamine. Excess triethylamine beyond this range would have little effect and under the suggested two equivalents would lead to poor yield.

Next, an acylating agent, preferably acetyl chloride, is dissolved in an acceptable ether solution, preferably tetrahydrofuran, and the third solution is combined at the first temperature added to the acetyl chloride solution to form a fourth solution at a first temperature. It is preferable that about five equivalents of acetyl chloride be used although at least two equivalents of acetyl chloride is added to the third solution at the first temperature with an acceptable range being two to ten equivalents of acetyl chloride. Excess acetyl chloride beyond this range would lead to a more complex product mixture. The third solution should be added dropwise into the acylating agent; otherwise, yields can be diminished.

The fourth solution now containing baccatin III is next stirred for a suitable interval, to allow the reaction to proceed preferably to completion. This interval should be at lest one-half hour, but an interval of up to twenty-four hours is desired to maximize yield. After stirring the fourth solution at the first temperature it is quenched with a suitable quenching compound that is effective to eliminate excess acylating agent therefrom to produce a fifth solution containing baccatin III. The preferable quenching compound is ammonium chloride solution. The fifth solution is then diluted with ethyl acetate to form an organic phase containing baccatin III and an aqueous phase. The aqueous phase discarded, and the organic phase is then washed with one normal HCl and brine, reduced in vacuo to a first residue. The first residue is then purified by column chromatography to get substantially pure baccatin III. Recrystallization may also be employed to purify the baccatin III.

Yields from this process indicate that approximately forty percent to eighty-five percent of the 10-deacetylbaccatin III is converted to baccatin III with about five percent of the C-7 acetate of baccatin III also being formed.

While it is preferred that tetrahydrofuran be the solvent into which the 10-deacetylbaccatin III be first dissolved, other ether solvents, including polyethers may be acceptable. While lithium chloride is the preferred lithium salt, it should be noted that lithium iodide also works well; however, the product mixtures that are obtained using lithium iodide are more complex. Further, while the preferred acylating agent is acetyl chloride, it should be possible to use acetic anhydride or acetyl bromide or other suitable acylating agent although it would be expected that the reaction may proceed at different rates.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

We claim:

1. A method of acylating 10-deacetylbaccatin III at a C-10 position over a C-7 hydroxy position thereof, comprising the steps of:
    (a) dissolving a selected quantity of 10-deacetylbaccatin III in an acceptable ether solvent therefor to form a first solution;
    (b) mixing a solution containing a lithium salt into the first solution to form a second solution;
    (c) adding a base selected from a group consisting of trialkyl amine bases and pyridine to the second solution thereby to form a third solution; and
    (d) combining the third solution with an acylating agent to form a fourth solution such that baccatin III is formed in the fourth solution.

2. A method according to claim 1 wherein approximately one equivalent of lithium salt in solution is added to the first solution to form the second solution.

3. A method according to claim 2 wherein the lithium salt is dissolved in tetrahydrofuran.

4. A method according to claim 1 wherein approximately two equivalents of the base is added to the second solution to firm the third solution.

5. A method according to claim 1 wherein the third solution is added to a solution containing the acylating agent to form the fourth solution.

6. A method according to claim 1 including the step of stirring the fourth solution for a period of at least one-half hour.

7. A method according to claim 1 including the step of quenching the fourth solution with a suitable quenching compound that is effective to eliminate excess of said acylating agent therefrom to produce a fifth solution.

8. A method according to claim 7 including the step of diluting said fifth solution with ethyl acetate to form an organic phase and an aqueous phase.

9. A method according to claim 8 including the step of washing the organic phase with one normal HCl and brine thereafter reducing the organic phase to a first residue.

10. A method according to claim 9 including the step of purifying the first residue to afford baccatin III.

11. A method according to claim 1 wherein said ether solvent is selected from a group consisting of: tetrahydrofuran and polyethers.

12. A method according to claim 1 wherein said ether solvent is anhydrous.

13. A method according to claim 1 wherein said acylating agent is acetyl chloride.

14. A method according to claim 1 wherein said quenching compound is ammonium chloride solution.

15. A method according to claim 1 wherein the steps are performed at a temperature of between −10° C. and 30° C.

16. A method according to claim 1 wherein one to two equivalents of a lithium salt, dissolved in tetrahydrofuran, is mixed into the first solution to form a second solution at the first temperature.

17. A method according to claim 1 wherein 1.1 equivalents of a lithium salt, dissolved in tetrahydrofuran, is mixed into the first solution to form the second solution.

18. A method according to claim 1 wherein said lithium salt is selected from a group consisting of lithium chloride and lithium iodide.

19. A method according to claim 18 wherein said lithium salt is lithium chloride.

20. A method according to claim 1 wherein two equivalents of said base are mixed into the second solution to form a third solution.

21. A method according to claim 20 wherein about five equivalents of said base are mixed into the second solution to form a third solution.

22. A method according to claim 21 wherein said base is triethyl amine.

23. A method according to claim 1 wherein the third solution is added to a solution of two to ten equivalents of acylating agent to form the fourth solution.

24. A method according to claim 23 wherein about five equivalents of the acylating agent is dissolved in THF into which the third solution is added to form a fourth solution.

25. A method according to claim 1 wherein said fourth solution is stirred for about twenty-four hours.

26. A method of acylating 10-deacetylbaccatin III at a C-10 position over a C-7 hydroxy position thereof, comprising the steps of:
  (a) dissolving a selected quantity of 10-deacetylbaccatin III in an acceptable ether solvent therefor to form a first solution at a first temperature;
  (b) mixing a solution of at least one equivalent of a lithium salt in tetrahydrofuran into the first solution to form a second solution;
  (c) adding at least an equivalent of a base selected from a group consisting of trialkyl amine bases and pyridine to the second solution to form a third solution;
  (d) adding the third solution at a first temperature to a solution of acylating agent in an acceptable ether solvent to form a fourth solution;
  (e) stirring the fourth solution for a selected interval of time;
  (f) quenching the fourth solution with a suitable quenching compound that is effective to eliminate excess of said acylating agent therefrom to produce a fifth solution;
  (g) diluting said fifth solution with ethyl acetate to form an organic phase and an aqueous phase;
  (h) washing said organic phase with HCl and brine;
  (i) reducing in vacuo said organic phase to a first residue; and
  (j) purifying said first residue to afford baccatin III.

27. A method according to claim 26 wherein said first temperature is between −10° C. and 30° C.

28. A method according to claim 26 wherein said lithium salt is selected from a group consisting of lithium chloride and lithium iodide.

29. A method according to claim 26 wherein said fourth solution is stirred for one-half to twenty-four hours.

* * * * *